(12) United States Patent
Steinkogler

(10) Patent No.: US 8,388,598 B2
(45) Date of Patent: Mar. 5, 2013

(54) METHOD AND DEVICE FOR CONTROLLING SEVERAL INFUSION PUMPS

(75) Inventor: Alexander Steinkogler, Munich (DE)

(73) Assignee: B. Bruan Medizinelektronik GmbH & Co. KG, Puchheim (DE)

( * ) Notice: Subject to any disclaimer, the term of this patent is extended or adjusted under 35 U.S.C. 154(b) by 0 days.

(21) Appl. No.: 11/920,287

(22) PCT Filed: May 11, 2006

(86) PCT No.: PCT/EP2006/062238
§ 371 (c)(1),
(2), (4) Date: Mar. 3, 2009

(87) PCT Pub. No.: WO2006/122903
PCT Pub. Date: Nov. 23, 2006

(65) Prior Publication Data
US 2009/0177188 A1    Jul. 9, 2009

(30) Foreign Application Priority Data
May 14, 2005    (DE) .......................... 10 2005 022 428

(51) Int. Cl.
*A61M 31/00*    (2006.01)
*A61M 37/00*    (2006.01)
*A61K 9/22*    (2006.01)
*F04B 49/00*    (2006.01)
*F04B 41/06*    (2006.01)

(52) U.S. Cl. ..................... 604/503; 604/890.1; 604/131; 604/65; 604/500; 604/67; 417/1; 417/5; 417/216

(58) Field of Classification Search ............... 604/890.1, 604/131, 65, 67, 66; 370/475; 417/1, 2, 417/5–7, 426, 270, 278, 286, 4; 700/282
See application file for complete search history.

(56) References Cited

U.S. PATENT DOCUMENTS

| | | | | |
|---|---|---|---|---|
| 4,966,579 A | * | 10/1990 | Polaschegg | 604/65 |
| 5,188,063 A | * | 2/1993 | Evans | 119/165 |
| 5,188,603 A | * | 2/1993 | Vaillancourt | 604/131 |
| 5,338,157 A | * | 8/1994 | Blomquist | 417/2 |
| 5,901,150 A | * | 5/1999 | Jhuboo et al. | 370/475 |
| 2002/0150476 A1 | * | 10/2002 | Lucke et al. | 417/2 |
| 2005/0085760 A1 | | 4/2005 | Ware | |

FOREIGN PATENT DOCUMENTS

| | | |
|---|---|---|
| EP | 0 906 767 | 4/1999 |
| EP | 0 960 627 A | 12/1999 |
| JP | 11104237 A | 4/1999 |
| JP | 11347118 A | 12/1999 |
| JP | 2001212230 A | 8/2001 |
| JP | 2004097757 A | 4/2004 |
| WO | WO 03/038566 A | 5/2003 |

OTHER PUBLICATIONS

International Search Report, Aug. 2, 2006.

* cited by examiner

*Primary Examiner* — Kevin C Sirmons
*Assistant Examiner* — Bradley G Thomas, Jr.
(74) *Attorney, Agent, or Firm* — RatnerPrestia

(57) ABSTRACT

The invention concerns a method and device for controlling a number of infusion pumps 2-10, whereby each infusion pump (2-10) has an infusate assigned to it which is administered within a pre-determinable period of time assigned to it as an infusion at a pre-determinable infusion rate to a living being, whereby the infusion pumps (2-10) exchange control data for activating and deactivating the various infusions in a chronologically coordinated manner autonomously.

17 Claims, 4 Drawing Sheets

METHOD AND DEVICE FOR CONTROLLING SEVERAL INFUSION PUMPS

This is a U.S. National Phase filing of PCT Application PCT/EP2006/06228 with an International Filing Date of May 11, 2006.

The invention concerns a method and device for controlling several infusion pumps, whereby each infusion pump has an infusion substance allocated to it which is fed to a living being within a pre-determinable time allocated to it as an infusion at a pre-determinable rate of infusion as in the preambles to patent claims 1 and 14.

In hospitals and other medical establishments, it is usual to give medication and/or pharmaceuticals, vitamins, nutrients, drugs, enzymes, metabolism products and the like to critically ill patients via what are known as infusion pumps intravenously, that is, directly into the blood, into the body tissues, the digestive tract, the respiratory system, onto mucous membranes or the skin. Infusion pumps are available essentially in the market in two designs. The first are injection pumps, which move an injection piston at a controlled rate of advance and so give the injection contents intravenously. Secondly, there are common pumps which give patients infusion liquids at a controlled rate from an infusion bottle or infusion bag at a higher level.

As it is now established clinical practice that medication and pharmaceuticals are no longer given via manual injection, but foreseeable drug administrators are prepared for infusion pumps and administered to the patient via these, such infusion pumps must work highly precisely and reliably if treatment is to succeed. Medication is often administered at a constant rate of flow or also intermittently, or with the aid of a rate of flow profile at variable rates, using systems or devices with a multiplicity of infusion pumps which may typically number ten or more at a typical intensive care bed. Twenty or more infusion pumps may even be used in intensive care for critically ill patients, such as when treating patients with cardiac diseases.

To date, such infusion pumps are controlled and pre-programmed to operate as individual units: that is to say, each infusion pump is programmed individually, to activate or deactivate infusing a given infusion substance contained in that infusion pump, for example. This means operating and initiating each individual infusion pump separately. This also means there is no way of allowing for how different drugs may interact within one another when given to a patient, insofar as this is not done by the doctor in charge or nursing staff themselves.

Automatic or self-acting allowance for the effects of an infusion at a predetermined infusion rate, given over a given time, can conventionally only be brought about via the individual infusion pump and the infusate assigned to it. For example, the patient's physiological data required to monitor what effects the infusate is having on the patient must be received and/or input in each infusion pump individually to recalculate a new length of time, activating or deactivating an infusion or interrupting it based on that monitoring data specifically for that infusate and administering it to the patient accordingly. No account is taken of the effects of infusates from other infusion pumps involved in treatment.

To date, for example, to anaesthetise patients, propofol is given over two sections of time, first to reduce the infusion pain caused by the medication by giving a lower concentration and, second, to keep the patient anaesthetised for as long as possible without having to change the injection or bag by giving as high a concentration of the drug as possible. In general, this involves diluting the propofol such that it is given as a 1% solution within the first time segment, to mitigate the infusion pain within that time segment. As soon as the patient has lost consciousness, they are given a 2% propofol solution in a second time segment. Such a switch, from the 1% to the 2% propofol solution, is carried out by operating staff or by the infusion pump operator. Having the switch made by a human being runs the risk—especially in the hectic clinical day to day life—that the switch will not be made properly or at the right time, which presents a health risk to the patient. This is particularly true when using pharmacokinetic models as the basis for injection strategies, as the algorithms on which the models are based prescribe concentrations which are different from the quantities of propofol which are actually given if a mistake is made, which inevitably mean that the infusate and/or the drug as prescribed is given too slowly or too fast. This means that switching from one propofol solution to the other by using one bag or syringe with the 1% propofol solution to a second bag or syringe with the 2% propofol solution within an infusion pump presents a safety risk to the patient, as there may be a risk that the operating staff will not give the 1% propofol solution for long enough, so the patient suffers infusion pain if they are not anaesthetised sufficiently. If the 1% propofol solution is not given for long enough, this may in turn mean that the 2% propofol solution is given for too long. i.e. the patient is overdosed, with all the risks that involves.

Using two independently functioning infusion pumps with two differently diluted propofol solutions also presents safety risks for the patient when switching from one propofol solution to the other, as for example either the low concentration propofol solution will not be given for long enough, and the patient will start by suffering infusion pain and then be overdosed with the drug, or the high-concentration propofol solution will not be given for long enough, so the patient is not anaesthetised sufficiently.

A device is known from DE 38 17 411 C2 for giving multiple infusion solutions concentratedly, continuously and simultaneously, whereby conveyor lines administer the infusion solutions via an adapter via a common patient line. This carries the infusion solutions simultaneously and mixes them before administering them. The infusion pumps are not coordinated with one another in terms of their infusion rates or when infusions are given as a function of their actual values, although a program saved in the central control device pre-determines the conveyance rates of the individual infusion pumps.

The problem with the present invention is therefore to provide a method and device for controlling a number of infusion pumps which minimises the risk of incorrect inputs, requires little operation and is easy to use.

On the method side, this task is resolved by the characteristics of patent claim 1 and on the device side by the characteristics of patent claim 14.

One of the main points of the invention lies in the fact that, with a method and device for controlling a number of infusion pumps, whereby each infusion pump having one infusate assigned to it, which is given to a living being within a period of time assigned to it at a pre-determinable rate of infusion, the infusion pumps exchange control data to activate and deactivate the different infusions in coordination with one another of their own accord. A method such as in the invention makes it possible to activate and deactivate individual infusion pumps within an infusion pump device which means there is no need to operate each individual infusion pump at the correct time in the course of treatment to be given. This eliminates the risk of an incorrect input as the result of human error and hence the risk to the patient under treatment's health as far as possible. Instead, control data is sent automatically via the data lines connecting the individual infusion pumps to one or more preselected infusion pumps as seen as the length of time for which a first infusion is to run from that sending infusion pump has ended and a second infusion is to be administered to the patient from another infusion pump by activating it.

It is also conceivable that a number of simultaneous, chronologically overlapping infusions of a number of infusates could be given from different infusion pumps, the start and end times of the length of time within which the different infusions are to be administered to the patient being determined by the individual infusion pumps exchanging control data amongst themselves autonomously, without involving any operating personnel, using a preset programme or prior input of a control process based on a pharmacological model.

Likewise, two different medications or pharmaceutical active agents could be given to the patient from two different infusion pumps alternately but coordinated with one another in time. Treatment based on such a control process would make it possible to administer these two medications for an extended period without clinic staff needing to intervene to operate the infusion pumps.

Having the infusion pumps communicate makes it possible to take account of a chemical influence or an influence of the effects of the medications which are divided between the various infusion pumps—under a patient model, as the case may be—, that one of the infusion pumps can refuse to be selected, or to allow other infusion pumps to be selected, should it be found that administering the medications which are assigned to these infusion pumps as infusion pumps as infusates would have an adverse chemical reaction, such as precipitating the whole mixture or affect their effects on the patient adversely. Likewise, an infusion pump might suggest being combined with other infusion pumps or the medications assigned to them or allow a member of the operating staff to select it or them if that would have the maximum positive effect both in terms of their effects and in terms of their chemical reaction.

As well as treatment given by infusion, or alternatively to it, another infusion pump could be used, for example, to administer a solution of common salt to meet a lower rate of the KVO rate while no pharmaceuticals are being injected. The KVO rate is intended to ensure that the veins and hence access to the patient do not close up if no liquid is being injected via the process.

Control data are exchanged, either via a control module assigned to each infusion pump, which is preferably integrated in the infusion pump, directly between infusion pumps and processed within each individual infusion pump or via a central control device via which communications and/or data exchanged between individual infusion pumps is transmitted, forwarded and influenced as necessary. With this in mind, the individual control units or central control device have controls for at least entering a control process to control activating and deactivating the various infusions for not less than two infusion pumps. Such a control process preferably activates and/or deactivates and/or interrupts infusions from these two or more infusion pumps simultaneously.

In a preferred embodiment, activating and/or deactivating infusions in this way can be commenced via a common start control and ended via a common stop control. Alternatively, pressing the start control more than once could activate the different infusion pumps in turn. Conversely, pressing the stop control could deactivate the individual infusion pumps in a pre-determinable sequence.

This control process could be assigned to a treatment regime to be selected by the operating staff which is determined using a barcode process, for example, whereby the control units or central control device autonomously select those infusion pumps which can be assigned to the treatment regime on account of the infusates which they contain automatically or display them for operators to select. This automatically assigns the infusion pumps which already contain the infusates desired for the treatment regime, whereby this can be done as a function of the infusion rate desired and the volumes of infusates the infusion pumps contain and other parameters of individual infusion pumps such as their maximum possible rate of flow.

One of the infusion pumps preferably gives the living being a dilutant to a pharmaceutical active agent administered via another infusion pump: the control data exchanged here can bring about deactivating infusing the dilutant while continuing to activate the pharmaceutical. This makes it possible, by those infusion pumps which give the dilutant to an anaesthetic, such as propofol to the patient switching off autonomously, increasing the concentration and anaesthetic without any action on the part of the operating staff being required. Alternatively, by pressing a button briefly, the operating staff can switch off the infusion pump containing the dilutant once they have established that the patient has already lost consciousness, so that the anaesthetic concentration can be increased as the patient is no longer suffering infusion pain. This avoids confusing the anaesthetic concentrations in two different periods of time when using pharmacokinetic models.

The patient's measured or estimated physiological data can be entered in the control units or central control device or received on an ongoing basis during the course of treatment to adjust the infusion rates, the length of time each individual infusion is to run, activation and deactivation times and other infusion parameters as the case may be autonomously via predetermined program steps—including by transmitting control data to the infusion pumps involved.

As well as the control units within the individual infusion pumps and/or a central control device as the case may be, and controls, an infusion device for conducting such a method preferably has a display device, either on each infusion pump or as a central display device for displaying the control data, the living being's measured physiological data, infusion pump activation and deactivation times, the infusion time periods and/or infusion rate. This enables the operating staff to monitor the patient's treatment status on an ongoing basis at any time to abort the treatment prematurely, or extend the treatment, or change treatment parameters.

If using a central control device, in particular, the display device for displaying the infusion pumps present in the infusion device is preferably linked to the control unit or integrated with it, so that it can display the flow rates of a number of infusion pumps involved in a treatment regime simultaneously, as a common diagram, for example. The control unit would also be able to use the display device to reproduce the patient's measured and/or estimated physiological data as well as or instead of the rates of flow of the individual infusion pumps, giving a combined abstract display which relates more to what effects a treatment regime is having than flow rates.

Alarms for individual infusion pumps can also be made to the central control device such that an alarm is tripped if an infusion pump is about to run dry. Having infusion pumps exchange data as in the invention could preferably result in reducing the number of unnecessary alarms, if, for example, one infusion pump is about to run dry at its current rate of flow but that this will not happen because of the already known infusion pattern of another infusion pump in the system.

Further advantageous embodiments will be apparent from the sub-claims.

Benefits and suitabilities can be taken from the specification which follow in connection with the drawings, whereby FIG. 1 Is a diagrammatic representation showing a model arrangement of an infusion device with a number of infusion pumps as in an embodiment of the invention;

Figure 1:
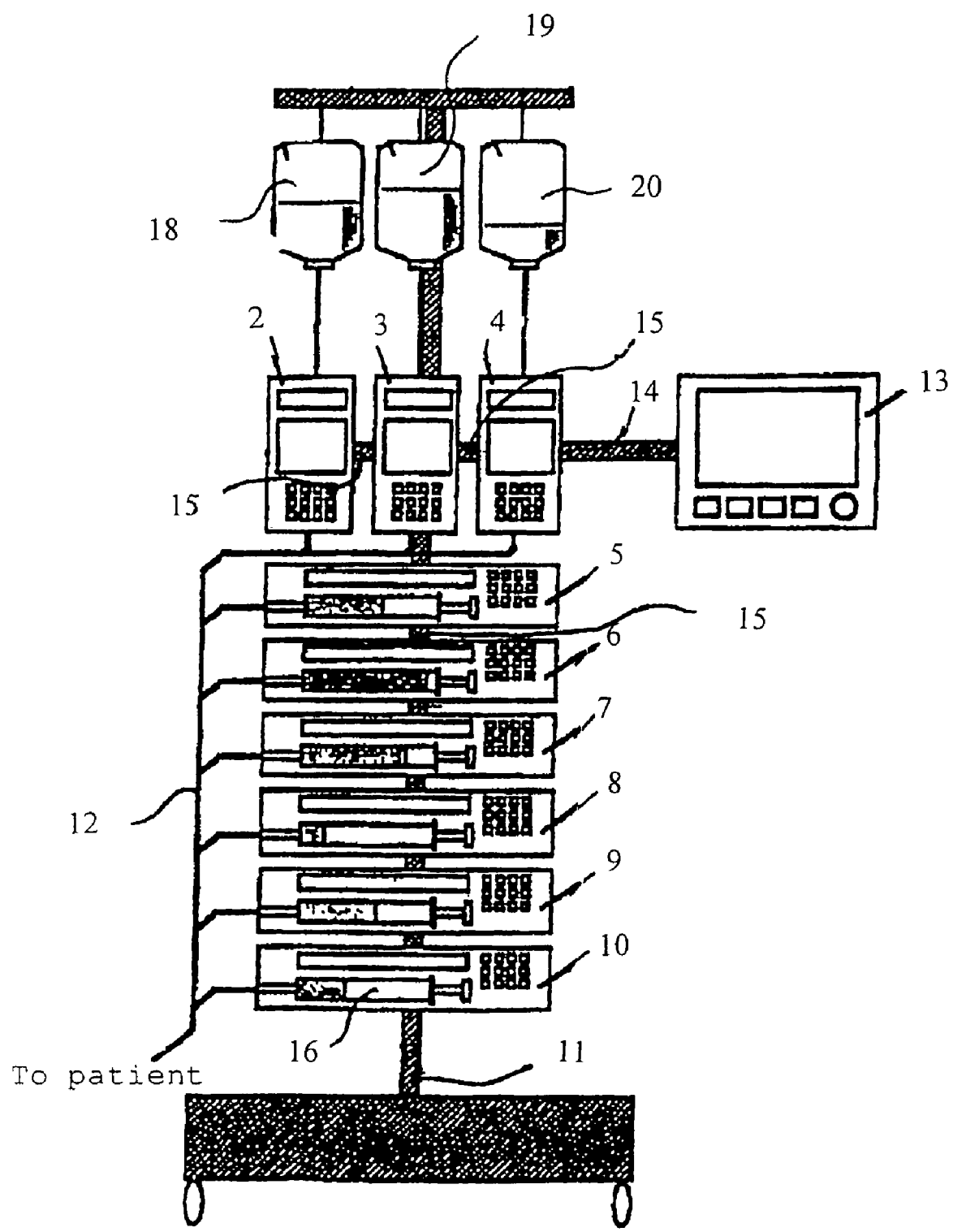

FIG. 1 is a diagrammatic representation showing the arrangement of an infusion pump device as in an embodiment of the invention. The infusion pump device 1 comprises infusion pumps 2-10, infusion pumps 5-10 being injection pumps.

The infusion pumps are arranged on a common column 11 of an infusion pump holder. The individual infusion pumps 2-10 can be arranged spatially on such a holder or some other design of holder more or less at will, provided the individual infusion pumps are connected by data lines, which can be arranged inside column 11. Such connections can be made both serially and star-shaped to transmit control data to the other infusion pumps in each case.

Instead of a cable connection, data may advantageously be sent wirelessly. this could be done, for example, via modulated ultrasound waves, modulated light waves (e.g. IrDa) or via radio waves (e.g. Bluetooth).

A central control device 13 with a display device can be arranged on one holder section 14, instead of or in addition to individual control units arranged within the individual infusion pumps, which are not shown in more detail here. This control and display device can be used to programme, operate and monitor all infusion pumps centrally, particularly in terms of the control data they exchange to activate and/or deactivate individual infusions of these infusion pumps 2-10.

Data connections running within column sections 15 between infusion pumps carry the control data required to control the mutual interdependency of a sliding movement of syringes 16 of the infusion pumps which takes place or not.

Each infusion pump has a keyboard 17 for entering additional parameters, such as the patient's physiological parameters or for programming the control unit within the infusion pump.

There are also fluid reservoirs 18, 19 and 20. A common infusion line 12 feeds the common infusion mixture to the patient.

As the medication patients in intensive care require varies while they are in intensive care, such an infusion device, with a multiplicity of infusion pumps, should be regarded as a dynamic system to or from which system components can be added or removed on the run and which can be used to adjust operating parameters, such as drugs to be administered, dosages to be given, administration times and the like on the run. This means that the patient's physiological data which is measured on an ongoing basis must be detected automatically, which can be done by a measured data line from the patient to the individual control units or the central control device which is not shown in more detail here.

In addition, or alternatively, pharmacokinetic models can be saved in the infusion device, whereby such models simulate how a drug once given is distributed in the patient's body through using suitable modelling. These models are drug-specific, and include other input parameters, like the patient's weight or age. The target variables are such things as a desired plasma level in the patient's blood, that is, a desired concentration of that drug in the blood. This target concentration can be constant over time, which means it merely replaces the volume of the drug which the body absorbs over time, or it can be variable over time.

Using a pharmacokinetic model, it is now possible, using a control algorithm, to control the individual infusion pumps' rate of flow such that the concentration of that drug in the blood is equal to the target concentration. Such a pharmacokinetic model can be implemented both in a control unit of each infusion pump itself or in the central control device 13.

The infusion pumps linked to one another via exchangeable control data can transmit a prescription sheet, which doctors usually complete manually to date, containing the drug prescriptions entered, with the care staff administering the medication as dosages during the course of a day, to the control units in the infusion pumps automatically, in that these have one or more interfaces within their data connection network to establish a connection to an overall data processing device in which the prescription schedule is entered instead of the prescription sheet completed manually. Alternatively, the prescription schedule can be entered directly in the central control and/or display device or in one of the control units of the infusion pumps which are linked to one another for data purposes.

Figure 2:
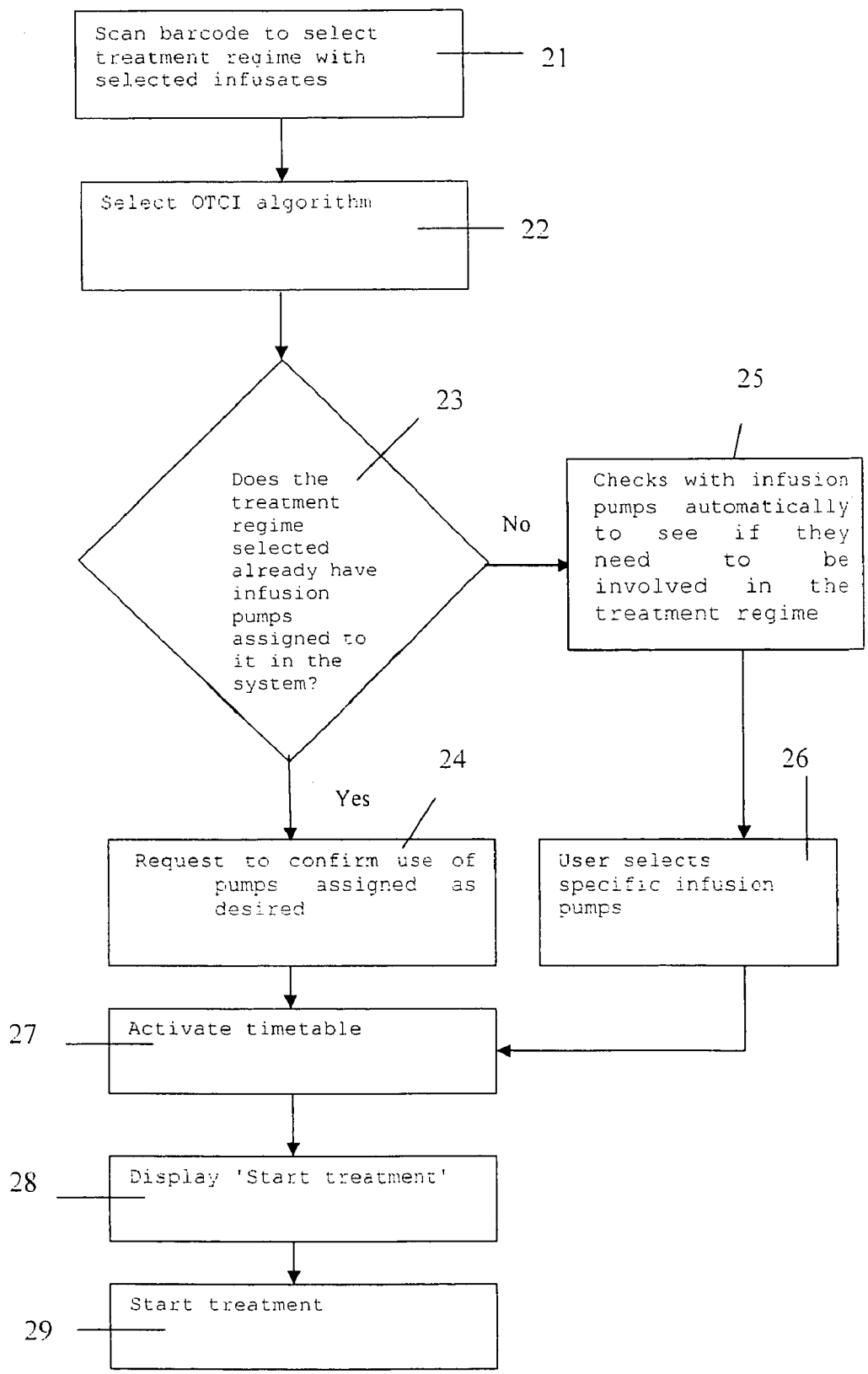
FIG. 2 Is a diagrammatic representation of a flowchart showing the process involved in the method as in the invention.

FIG. 2 is a diagrammatic flowchart showing the procedure as in the invention as in an embodiment of the invention. As in step 21, the infusion device instructs the operating staff, via the central display device or a display in one of the infusion pumps to run a barcode scan to select a given treatment, using a barcode scanner connected externally to the infusion pump to read barcodes assigned to individual treatment regimes.

In the present case, the treatment regime selected is anaesthetising a patient using propofol and a dilutant. Once such a propofol-dilutant treatment regime is selected, the infusion device or the individual infusion pump automatically establishes an associated OTCI algorithm for an infusion pump to be determined (step 22).

Step 23 establishes automatically whether the treatment regime selected already has pumps assigned to it within the infusion device and/or system. This can, for example, be made dependent on whether an infusion pump has already been filled with propofol and another infusion pump with the corresponding infusate.

Should such pumps already be on hand, step 24 then instructs the operating staff to confirm this assigned pump selection.

If no infusion pumps are assigned automatically in step 23, step 25 asks the control units of the individual infusion pumps which have been assigned of the infusates involved instead whether they should be involved in the treatment regime. Should the operating staff have selected the pumps offered as in step 26, a timetable will be activated as in step 27.

Such a timetable may, for example, instigate a simultaneous startup of a first infusion pump with propofol as the infusate and a second infusion pump with dilutant, such as fat-based. The two infusates are mixed and administered to the patient together, giving a propofol solution at a concentration of less than 1%, enabling the diluted propofol to be administered with little infusion pain.

As soon as the patient has lost consciousness, using the pre-determinable timetable, control data can be sent from the first infusion pump to the second infusion pump containing the dilutant, switching the second infusion pump off to administer the propofol at a higher concentration to keep the patient anaesthetised.

Should the doctor in charge or the operating staff wish to sbort the anaesthetising process prematurely, they can do so by pressing a button arranged on one of the two infusion pumps which switches both infusion pumps off simultaneously by transmitting control data between them.

Once the timetable has been activated, the infusion device or individual infusion pump displays 'Start treatment' as in step 28. Treatment then starts as in step 29.

Figure 3:
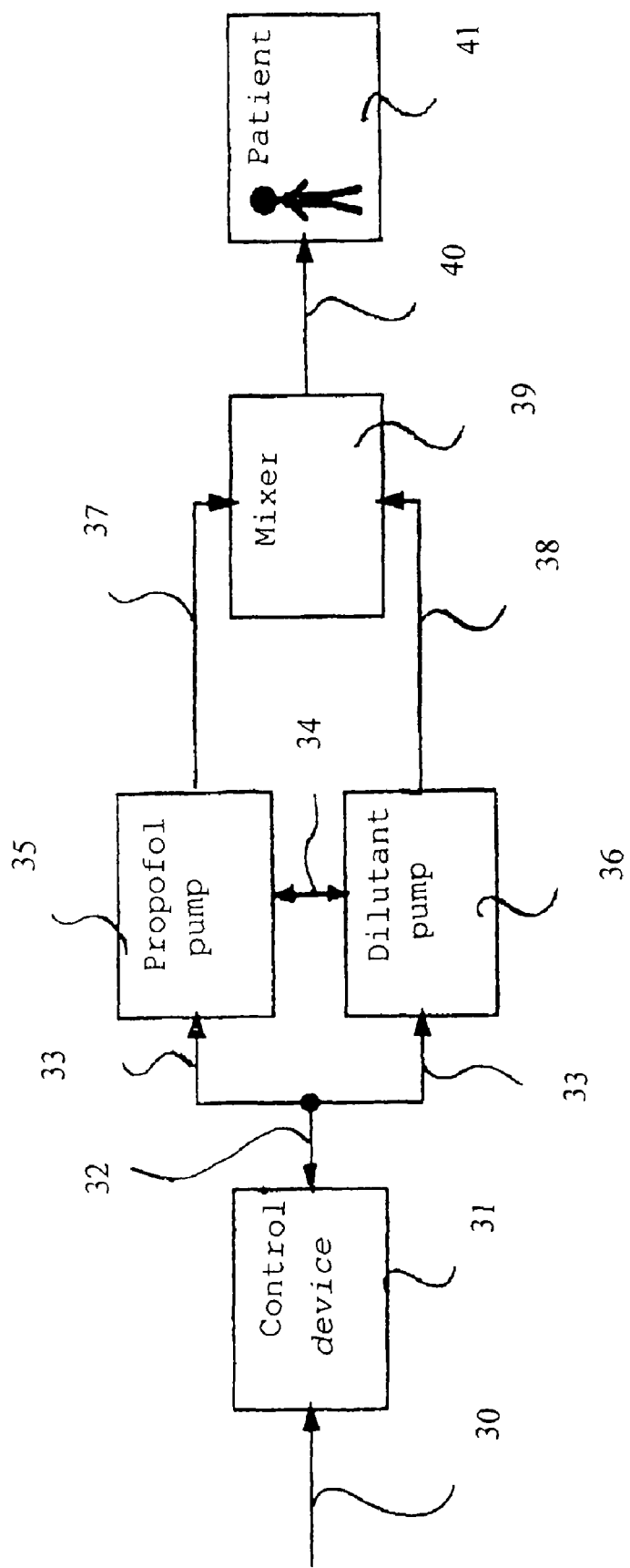
FIG. 3 Is a diagrammatic representation showing the method as in the invention using the device as in the invention as in an embodiment of the invention.

FIG. 3 is a diagrammatic representation showing ow the method as in the invention works by presenting the infusion device. Entering data, as indicated by arrow 30, in a central control device 31 pre-programmes the procedural sequence desired. in this case treatment with propofol. By control device 31 exchanging data interactively with an infusion pump 35 containing propofol and an infusion pump containing the dilutant for the anaesthetic propofol, infusion pumps 35 and 36 and central control device 31 communicate and infusion pumps 35 and 36 communicate in particular, as indicated by arrows 32, 33 and 34. This makes it possible to use programming and exchanging data between the infusion pumps, as double arrow 34 indicates, to switch the dilutant and hence infusion pump 36 off in time if the patient 41 is anaesthetised sufficiently.

Both the propofol and dilutant are mixed until that time via lines 37, 38 within a mixer 39 and administered to patient 41 via a common line 40.

Figure 4:
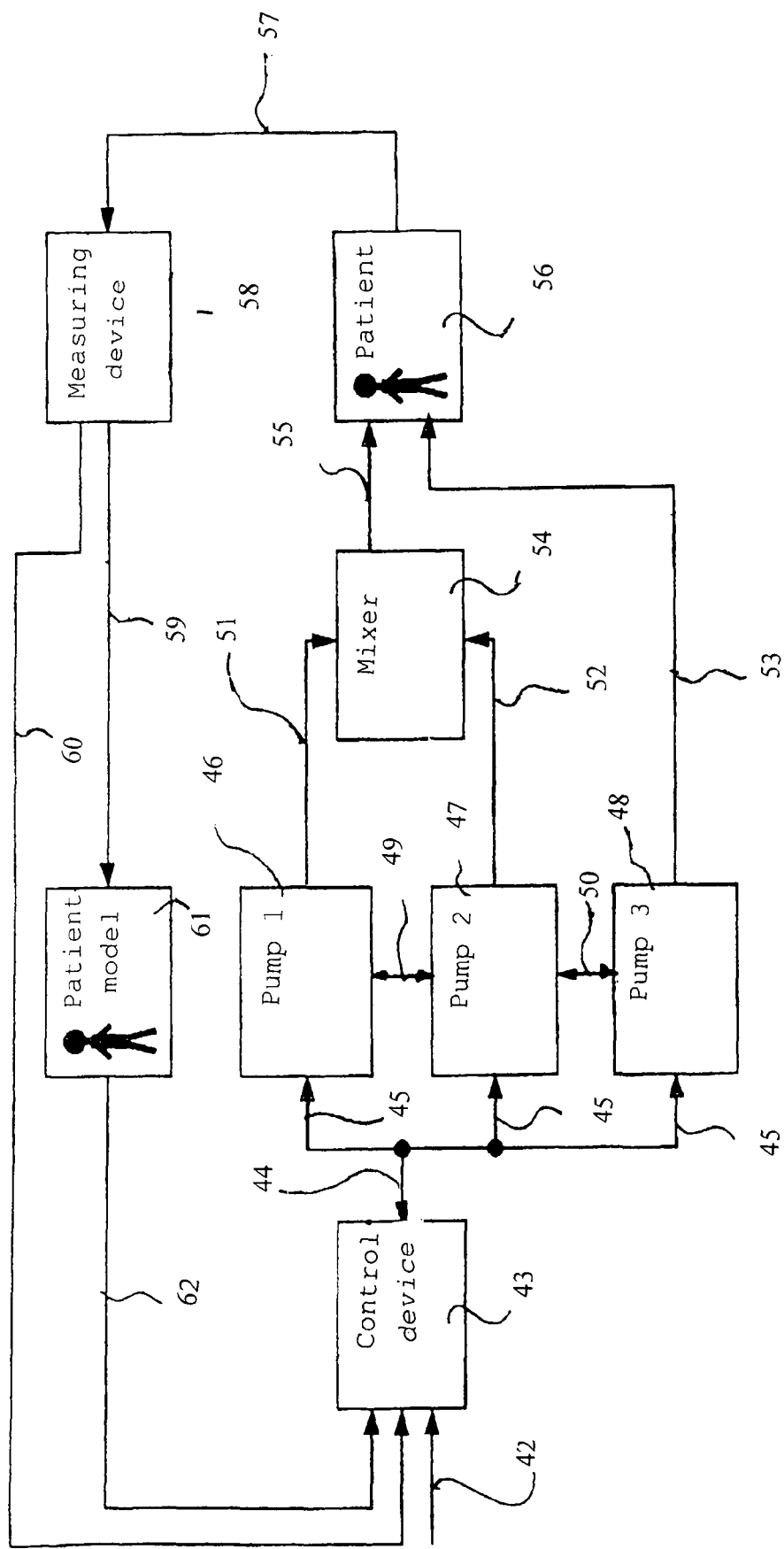
FIG. 4 Is a diagrammatic representation of the method using the device as in another embodiment of the invention.

FIG. 4 is a diagrammatic representation of the method as in the invention, using another infusion device. Once again, as shown by arrow 42, data for programming a control device 43 is entered and passed by exchanging data between the central control device 43 and individual fusion pumps 46, 47 and 48 via data exchange lines 44 and 45 to the infusion pumps, whereby infusion pumps 46, 47, 48 exchange this data with the central control device 43, to select suitable infusion pumps, for example, via lines 44 and 45 and in particular amongst themselves via lines 49, 50 to review a suitable combination of those infusion pumps.

Infusates from infusion pumps 46, 47 are taken via lines 51, 52 to a mixer 54, where they are mixed with one another and passed to a patient 56 via line 55 and via a line 53 from the infusion pump. The patient's physiological data are then measured via a measuring device 58 and a line 57.

The patient's measured data are fed back either directly via a connection 60 or indirectly via a patient model 61 via connections 59, 62 to the control device 43, which compares the measured physiological data with data as specified by patient model 61.

All characteristics disclosed in the application documents are claimed as essential to the invention insofar as they are new, individually or in combination, compared with the state of the art.

KEY TO DRAWINGS

1 Infusion device
2-10 Infusion pumps
11 Column
12 Infusion line
13 Central control device
14, 15 Column section
16 Syringes
17 Input elements
18, 19, 20 Liquid containers
21 Step: scanning barcode
22 Step: selecting OTCI algorithm
23 Step: allocating pumps
24 Step: instruction to confirm selected pumps
25 Step: enquire re infusion pumps available to be allocated
26 Step: select infusion pumps available to be allocated
27 Step: activate time schedule
28 Step: display 'Start treatment'
29 Step: start treatment
30, 42 Data input
31, 43 Central control device
32, 33, 34, 44, 45, 49, 50 Data exchange lines
35, 36, 46, 47, 48 Infusion pumps
37, 38, 40, 51, 52, 53, 55 Infusion lines
39, 54 Mixers
41, 56 Patient
57, 59, 60 Measured data transmission lines
58 Measuring device
61 Patient model
62 Comparing data from patient model with measured data

The invention claimed is:

1. A method for controlling several infusion pumps, each infusion pump having an infusate assigned to it which is administered to a living being for a pre-determinable period of time as an infusion at a pre-determinable infusion rate, the method comprising:
   originating control data at a first infusion pump using measured or estimated physiological data of the living being, the control data comprising instructions to activate a second infusion pump, wherein the originating step comprises:
      comparing the measured or estimated physiological data of the living being with a pharmacokinetic model at the first infusion pump, and
      automatically originating the control data at the first infusion pump based on results of the comparison;
   exchanging the control data between the first and second infusion pumps of their own accord for coordinating activating and deactivating the various infusions chronologically;
   receiving a first portion of the control data at the second infusion pump from the first infusion pump; and
   activating the second infusion pump in response to receipt of the first portion of the control data from the first infusion pump.

2. The method of claim 1, wherein each infusion pump processes the control data via a control unit assigned to it and sends it to at least one of the other infusion pumps.

3. The method of claim 1, wherein each infusion pump is connected to a central control device and processes control data via the central control device and processes control data via the central control device and sends it to at least one of the other infusion points.

4. The method of claim 3, wherein the central control device is composed of a number of individual control units.

5. The method of claim 1, wherein the infusion from at least one of the infusion pumps is always activated.

6. The method of claim 1, wherein the infusion from all infusion pumps is activated and/or deactivated simultaneously.

7. The method of claim 3, wherein controls on the central control device are usable to input at least one control process to control activating and deactivating the different infusions for at least two infusion pumps.

8. The method of claim 7, wherein the central control process activates and/or deactivates and/or interrupts the infusion by the two or more infusion pumps.

9. The method of claim 7, wherein selecting a treatment regime to which a control process is assigned selects the infusion pumps assignable to that treatment regime autonomously or displays them to an operator to select.

10. The method of claim 1, wherein at least one of the infusion pumps administers a dilutant to the living being in addition to a pharmaceutically active agent which is administered via another infusion pump.

11. The method of claim 1, wherein the control data deactivate the infusion of the dilutant while keeping the pharmaceutically active agent activated.

12. The method of claim 1, wherein a display device displays the infusion rates of the infusion pumps and/or measured or estimated physiological data of the living being and/or control data and/or activation and deactivation times of the infusion pumps and/or infusion periods.

13. A system for controlling a number of infusions, comprising:
a plurality of infusion pumps, each infusion pump having an infusate assigned to it which can be administered for a pre-determinable period of time as an infusion at a pre-determinable infusion rate to a living being, wherein control data for activating and deactivating the various infusions in chronologically coordinated fashion can be originated at a first infusion pump and exchanged between the first and a second infusion pump autonomously, the control data comprising instructions to activate the second infusion pump;
a first control unit in the first infusion pump, the first control unit transmitting a first portion of the control data; and
a second control unit in the second infusion pump, the second control unit receiving the first portion of control data from the first control unit and activating the second infusion pump in response to receipt of the first portion of control data from the first infusion pump,
wherein the first infusion pump is programmed to compare measured or estimated physiological data of the living being with a stored pharmacokinetic model, and automatically originate the control data at the first infusion pump based on results of the comparison.

14. The system of claim 13, wherein each infusion pump has one of the control units which processes the control data and sends it directly to control units of other infusion pumps.

15. The system of claim 13, wherein the infusion pumps and the transmission of control data between the infusion pumps are controlled chronologically dependent on one another.

16. The system of claim 13, further comprising controls on the infusion pumps for entering control commands, selecting control processes, selecting infusion pumps involved in those control processes and/or entering physiological data from the living being.

17. The system of claim 13, further comprising a display device on each infusion pump for displaying control data, measured or estimated physiological data of the living being, the times when infusion pumps are activated and deactivated, infusion periods and/or infusion rates.

* * * * *

UNITED STATES PATENT AND TRADEMARK OFFICE
CERTIFICATE OF CORRECTION

PATENT NO. : 8,388,598 B2  
APPLICATION NO. : 11/920287  
DATED : March 5, 2013  
INVENTOR(S) : Alexander Steinkogler Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 320 days.

Signed and Sealed this

First Day of September, 2015

Michelle K. Lee
*Director of the United States Patent and Trademark Office*